United States Patent [19]
Abiuso

[11] Patent Number: 5,433,706
[45] Date of Patent: Jul. 18, 1995

[54] PERFUSION BALLOON CATHETER

[75] Inventor: Christopher L. Abiuso, Pembroke Pines, Fla.

[73] Assignee: Cordis Corporation, Miami Lakes, Fla.

[21] Appl. No.: 142,721

[22] Filed: Oct. 25, 1993

[51] Int. Cl.$^6$ ............................................. A61M 29/00
[52] U.S. Cl. .................................. 604/96; 604/101; 606/194
[58] Field of Search .................. 604/96, 95, 101, 102, 604/103, 264, 281; 606/194

[56] References Cited

U.S. PATENT DOCUMENTS

| | | |
|---|---|---|
| 3,889,686 | 6/1975 | Duturbure . |
| 4,183,102 | 1/1980 | Guiset . |
| 4,233,983 | 11/1980 | Rocco ................................ 604/102 |
| 4,423,725 | 1/1984 | Baran et al. . |
| 4,447,227 | 5/1984 | Kotsanis . |
| 4,581,017 | 4/1986 | Sahota ................................ 604/101 |
| 4,585,000 | 4/1986 | Hershenson . |
| 4,641,653 | 2/1987 | Rockey . |
| 4,694,827 | 9/1987 | Weiner et al. . |
| 4,723,549 | 2/1988 | Wholey et al. . |
| 4,762,130 | 8/1988 | Fogarty et al. . |
| 4,763,653 | 8/1988 | Rockey . |
| 4,771,777 | 9/1988 | Horzewski et al. . |
| 4,787,388 | 11/1988 | Hofmann . |
| 4,790,315 | 12/1988 | Mueller, Jr. et al. . |
| 4,795,427 | 1/1989 | Helzel . |
| 4,820,271 | 4/1989 | Deutsch . |
| 4,832,028 | 5/1989 | Patel . |
| 4,857,054 | 8/1989 | Helfer . |
| 4,877,031 | 10/1989 | Conway et al. . |
| 4,878,495 | 11/1989 | Grayzel . |
| 4,892,519 | 1/1990 | Songer et al. . |
| 4,909,252 | 3/1990 | Goldberger . |
| 4,958,634 | 9/1990 | Jang ................................ 604/103 X |
| 4,983,165 | 1/1991 | Loiterman ........................... 604/101 X |
| 4,983,167 | 1/1991 | Sahota . |
| 5,000,734 | 3/1991 | Boussignac et al. . |
| 5,000,743 | 3/1991 | Patel . |
| 5,006,119 | 4/1991 | Acker et al. . |
| 5,019,042 | 5/1991 | Sahota . |
| 5,035,694 | 7/1991 | Kasprzyk et al. . |
| 5,046,503 | 9/1991 | Schneiderman . |
| 5,078,685 | 1/1992 | Colliver . |
| 5,087,247 | 2/1992 | Horn et al. . |
| 5,090,958 | 2/1992 | Sahota . |
| 5,090,960 | 2/1992 | Don Michael . |
| 5,108,370 | 4/1992 | Walinsky . |
| 5,129,883 | 7/1992 | Black . |
| 5,135,474 | 8/1992 | Swan et al. . |
| 5,137,513 | 8/1992 | McInnes et al. . |
| 5,147,377 | 9/1992 | Sahota . |
| 5,152,277 | 10/1992 | Honda et al. . |
| 5,160,321 | 11/1992 | Sahota . |
| 5,181,911 | 1/1993 | Shturman . |
| 5,195,955 | 3/1993 | Don Michael . |
| 5,195,971 | 3/1993 | Sirhan . |
| 5,222,941 | 6/1993 | Don Michael . |
| 5,226,888 | 7/1993 | Arney . |
| 5,232,446 | 8/1993 | Arney . |
| 5,261,879 | 11/1993 | Brill . |

*Primary Examiner*—John D. Yasko
*Attorney, Agent, or Firm*—Lockwood, Alex, Fitzgibbon & Cummings

[57] ABSTRACT

A catheter suitable for percutaneous translumenal coronary angioplasty procedures is provided. The catheter includes a balloon member having an interior and exterior surface and having at least one longitudinal portion bonded to a flexible tube. The balloon includes a collapsed condition of a size allowing it to be transported through a body vessel and an expanded condition of a size allowing it to engage a body vessel wall. The balloon in its expanded condition defines longitudinal passageways for perfusing blood past the balloon.

6 Claims, 1 Drawing Sheet

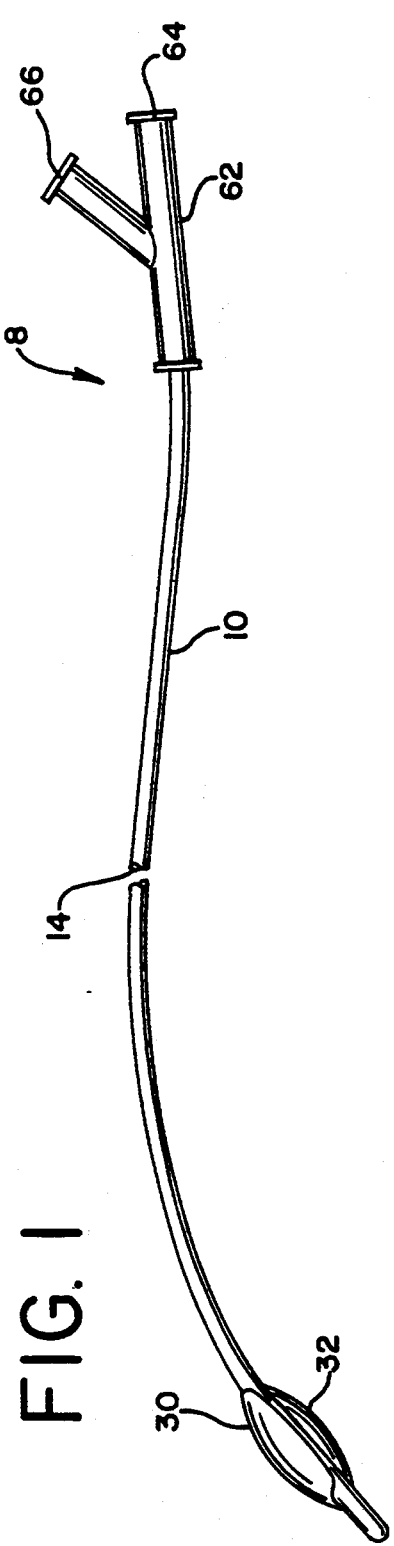
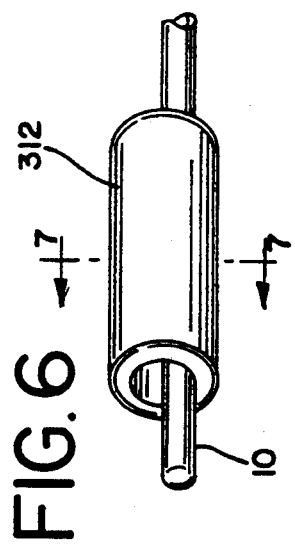
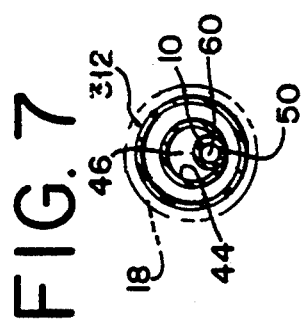
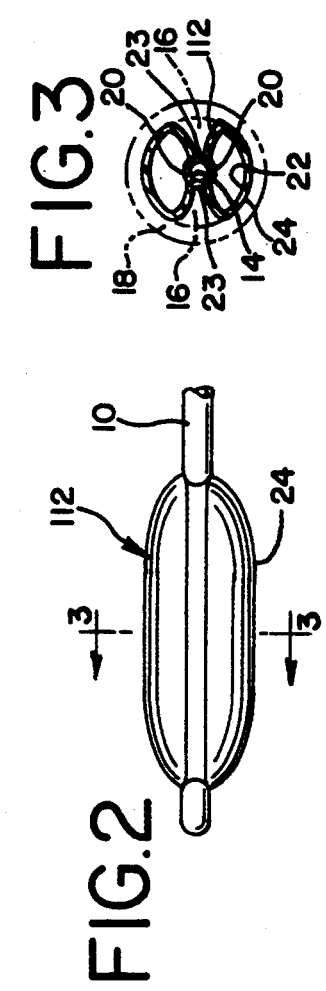
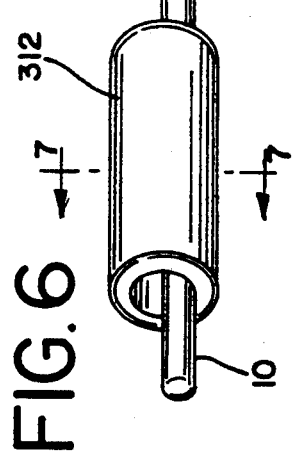
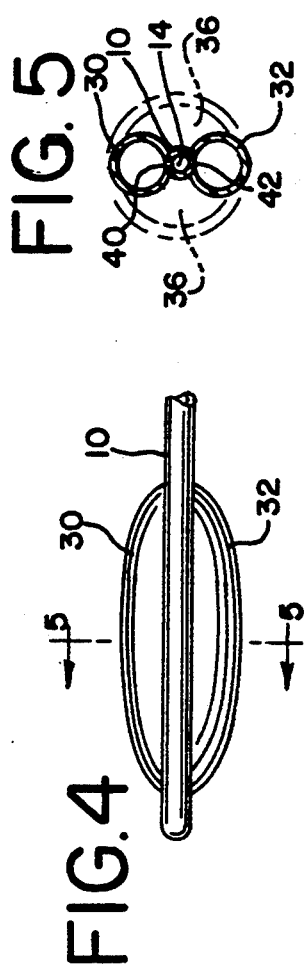

PERFUSION BALLOON CATHETER

The present invention relates generally to dilation catheters suitable for percutaneous transluminal coronary angioplasty procedures (PTCA), and more particularly to dilation catheters for use in PTCA procedures wherein blood is perfused distally of the dilation balloon during the inflation cycle of the balloon.

BACKGROUND AND SUMMARY OF THE INVENTION

PTCA procedures generally include inflation of a balloon in an arterial passage in an effort to clear a flow path for blood by dilating the stenosis. Inflation of the balloon and subsequent deflation and removal of the balloon results in treatment of the stenosis to increase the available cross-sectional area for blood to flow through the arterial passage.

In typical PTCA procedures, a guiding catheter is inserted into the cardiovascular system through the Tee-brachial or femoral arteries, generally under local anesthesia, until the distal tip of the catheter is in a coronary artery and generally positioned adjacent a stenosis. An extensible balloon of a dilation catheter is advanced through the guiding catheter alone or over a previously introduced guidewire until the balloon is positioned across the stenosis. The balloon is then inflated to a predetermined size with a fluid, preferably a radiopaque liquid, to radially compress the inside of the artery wall, thereby dilating the lumen of the artery. The balloon is then deflated so that the dilation catheter can be removed, and blood flow resumed through the dilated artery that now has a larger cross-sectional area to permit a greater volume of blood to flow therethrough.

In typical PTCA procedures, when the balloon of a dilation catheter is inflated in a coronary artery, all flow ceases through the coronary artery. If blood flow ceases for too long a period of time, the part of the heart which that coronary artery serves can begin to suffer from lack of blood, or ischemia. If the balloon remains inflated in the artery for prolonged periods of time, the injury caused by the absence of blood flow can be irreversible in some cases. On the other hand, it has been found that the probability of an artery wall or the stenosis maintaining its dilated cross-sectional area after having been subjected to dilation from an extensible balloon is directly related to the length of time that the balloon is inflated while located across the stenosis. However, the aforementioned potential problems associated with blocking blood flow are increased the longer the balloon is inflated in the artery.

Attempts have been made to produce dilation catheters that perfuse blood through a catheter or balloon when the balloon is inflated to avoid ischemia conditions distally of the balloon. For example, Wejay, et al., U.S. Pat. No. 5,158,540, disclose a perfusion catheter that perfuses blood during the balloon's inflation cycle to allow for longer inflation periods; however, the catheter is extremely complicated structurally and expensive to manufacture.

It is, therefore, a general object of the present invention, to provide a new and improved perfusion balloon dilation catheter suitable for PTCA procedures.

Another object of the invention is to provide a dilation catheter suitable for PTCA procedures wherein the catheter perfuses blood around the inflated balloon and permits prolonged inflation times for the balloon.

Yet another object of the present invention is to provide a dilation catheter of a relatively simple structure for use in PTCA procedures where blood is perfused distally of the inflated balloon.

The present invention overcomes the problems associated with the prior art perfusion catheters by providing a perfusion balloon catheter, including a flexible tubular member, and at least one annularly shaped extensible balloon member having an exterior surface and an interior surface. The interior surface of the balloon member is communicatingly connected to the outer surface of the flexible tubular member. Portions of the exterior surface remain adjacent the flexible tube while other portions of the exterior surface are spaced from the flexible tube when the balloon is inflated. Means are provided for inflating the balloon member radially outwardly from the tubular member, such that when the balloon is disposed in an artery, at least one longitudinal pathway is formed between the flexible tubular member, the artery wall and portions of the inflated balloon.

For a complete understanding of the present invention, reference is made to the embodiments illustrated in greater detail in the accompanying drawings and described by way of example. It should be understood that this invention is not limited to the particular embodiments illustrated herein, but is defined by the appended claims.

BRIEF DESCRIPTION OF THE DRAWINGS

FIG. 1 is a plan view of a balloon catheter made according to the present invention;

FIG. 2 is a plan view of an alternative embodiment of a distal end portion of a catheter made according to the present invention;

FIG. 3 is a cross-sectional view along the line 3—3 of FIG. 2;

FIG. 4 is a plan view of the distal end portion of the catheter of FIG. 1 made according to the present invention;

FIG. 5 is a cross-sectional view along the line 5—5 of FIG. 4;

FIG. 6 is a perspective view of an alternative embodiment of the distal end portion of a catheter made according to the present invention; and FIG. 7 is a cross-sectional view along the line 7—7 of FIG. 6.

DETAILED DESCRIPTION OF THE PREFERRED EMBODIMENT

As illustrated in the drawings, the perfusion balloon catheter, generally designated at 8 in FIG. 1, made according to the present invention comprises an elongated flexible tubular shaft 10 with an inflatable balloon structure located substantially near the distal end of the shaft. Lumen 14 is formed in the shaft 10 and may be of a substantially small diameter similar to that of a standard guidewire preferably having a diameter of between about 0.008 and about 0.020 inch. Lumen 14 is utilized for carrying fluid, such as a radiopaque saline solution or other fluid of a type well known in the art which is communicated through lumen 14 to the balloon area for inflating and deflating the balloon structure. The diameter of lumen 14 is large enough to carry sufficient amounts of fluid for inflating the balloon. Flexible tubing 10 utilized in the present invention is preferably formed of a suitable thermoplastic material, such as polyethylene, polyvinylchloride, and the like, or from stainless steel, or it can be composed of a composite structure. Fluid is communicated to the balloon interior through openings, shown at 20 in FIG. 3, in the shaft 10 between lumen 14 and the balloon interior. It is preferred that the same number of openings 20 be utilized for each balloon so that the diametrically opposed portions of the balloon structure inflate evenly.

The balloon 112 which is depicted in FIGS. 2 and 3 is annularly shaped and has an interior surface 22 and a exterior surface 24. The balloon may be produced from material well known in the art, such as, irradiated polyethylene, polyethylene terephthalate, nylon, polyamide, or other suitable flexible but relatively inelastic material. Balloon 112 is bonded along generally opposing longitudinal portions of its interior surface 22 to the outer diameter of flexible tubing 10 forming a pair of elongated longitudinal walls 23. Portions of the interior surface 22 of balloon 112 are connected to the flexible tubing 10 in such a manner that when viewed in cross section, as in FIG. 3, there appear to be two separate diametrically opposed balloons, in a somewhat mushroom cap shape or circular ring sector shape. It is preferred that portions of the interior surface 22 of balloon 112 connected to the flexible tubing be diametrically opposed.

When inflated, portions of the exterior surface of balloon 112 extend radially outwardly from the flexible tubing over less than a 360° arc but engage a majority of the artery wall or stenosis. This configuration of balloon 112 allows the formation of a pair of longitudinal channels 16 which extend parallel to the flexible tubing on diametrically opposed sides and permit the perfusion of blood past the balloon while the balloon is inflated. Each of the channels 16 are defined by portions of balloon 112, elongated longitudinal wall 23 and the artery wall 18. The cross-sectional size of longitudinal passageways 16 may be varied by limiting or expanding the amount of the balloon's interior surface 22 which is bonded to the flexible tubing 10.

A second embodiment of the invention, shown in FIGS. 1, 4 and 5, includes flexible tubing 10, as described before, and at least two separate selectively inflatable balloons, 30 and 32, each separately bonded to the circumference of the flexible tubing, preferably on diametrically opposed sides. Balloons 30, 32 are preferably cylindrical in shape and are bonded along a longitudinal portion of their outer surface to the flexible tubing. It is preferred that the longitudinal portion of each balloon bonded to flexible tube 10 be bonded to less than one-half of the circumference of flexible tube 10. This is to insure that a longitudinal pathway will be formed when the balloon is inflated in the artery. Each balloon 30 and 32 communicates separately with the flexible tubing 10 through openings 40 and 42 respectively for the introduction of fluid. Balloons 30 and 32 are adapted to be radially expanded by the introduction of fluid into the flexible tubing which passes into the interior of each of the balloons 30 and 32 via openings 40 and 42. The fluid is pumped through lumen 14 by a reversible pump of a type well known in the art which is connected to the proximal end of flexible tubing 10. It should be understood that the present invention may be used on fixed wire, over-the-wire, and monorail type balloon catheters. As shown in FIG. 1, a y-shaped hub 62 of a type well known in the art may be utilized. The hub includes two openings 64, 66 either of which may be connected to a pump mechanism for introducing fluid into the flexible tube 10.

Expansion of each of the balloons 30, 32 when disposed in an artery or other body vessel forms longitudinal passageways 36 having boundaries defined by flexible tubing 10, a portion of each of the balloons 30 and 32, and the artery wall. The size and shape of balloons 30, 32 may be varied to adjust the size and cross-sectional area of the longitudinal passageways 36.

In a third embodiment, illustrated in FIGS. 6 and 7, flexible tubing 10 is eccentrically mounted to an annularly shaped balloon 312 along the balloon's inner diameter 44. Flexible tubing 10 includes a lumen 60 which communicates with balloon 312 through opening 50 to introduce fluid to the interior of the balloon to expand the balloon. Expansion of the balloon 312 against the artery walls 18 or stenosis dilates the artery and provides a passageway 46 defined by the inner diameter of the balloon and portions of the flexible tubing through the stenosa while the balloon is inflated. The size of the balloon may be varied, but should have a sufficient outer diameter when inflated to engage the stenosis or artery wall.

In operation, catheter 8 is generally advanced from the femoral artery or the Tee-brachial artery up the aortic root and is positioned in the appropriate coronary artery. Advancement of the catheter through an artery or vessel is preferably performed when the balloon structure is in a collapsed non-inflated condition. The balloon 112, which is disposed at the distal end of the catheter, is positioned across a restriction or stenosis in the artery. Thereafter, balloon 112 is inflated in the artery by pumping fluid through lumen 14 of flexible tubing 10. Inflation of the balloon causes the balloon to radially expand and engage the artery wall or stenosis and dilate the artery wall. Balloon 112 may remain in its expanded condition for a considerably longer time than conventional catheters because the blood is perfused past the balloon through longitudinal passageways 16 without need for a separate mechanism to pump or channel the blood. When utilizing catheter 8 made according to the present invention, particularly the embodiments shown in FIGS. 1-5, it may be desirable to rotate the balloon about its longitudinal axis to insure that the entire inner surface of the artery wall or stenosis is engaged by the inflated balloon. The doctor performing the PTCA procedure would insert the balloon and inflate it as before. This allows the balloon to engage a majority of the inner circumference of the artery wall or stenosis. To ensure that the area of the artery wall not initially engaged by the balloon is dilated (shown as 18 in FIG. 3.) the balloon is deflated and rotated between approximately 30°-90°. Balloon 112 is then reinflated to insure that the portion of the artery wall or stenosis not previously dilated is engaged by the inflated balloon. The balloon may be deflated, rotated, and reinflated as many times as is necessary.

After the perfusion catheter has performed its function of dilating the restricted artery, the balloon may be deflated and the catheter removed. It should be understood that the operation described above is equally applicable to any of the embodiments of the invention, as each allows perfusion of blood during balloon inflation cycles without the need for blood pumping mechanisms.

It will thus be seen that the present invention provides a new and useful perfusion balloon catheter having a number of advantages and characteristics, including those pointed out herein and others which are inherent in the invention. Preferred embodiments of the invention have been described by way of example, and it is anticipated that modifications may be made to the described form without departing from the spirit of the invention or the scope of the appended claims.

I claim:

1. A method of performing percutaneous transluminal angioplasty procedures utilizing a dilation catheter wherein said method comprises the steps of: providing a dilation catheter having an elongated flexible tube having a single extensible balloon disposed on said tube at a given location along its length, said single extensible balloon being bonded to the elongated tube at at least two locations to define at least two balloon member portions between at least two elongated longitudinal walls secured to the tubing, said balloon having a collapsed condition of a size allowing said dilation catheter to be transported through a body vessel and having an expanded condition of a size allowing said balloon member portions to engage a body vessel wall; inserting said dilation catheter in its collapsed condition into a body vessel; positioning said balloon adjacent a stenosis or restriction in said body vessel; inflating said balloon to its expanded condition for a predetermined period of time to a sufficient size until each balloon member portion engages said stenosis while simultaneously forming at least two longitudinal passageways defined between walls of the balloon; perfusing blood through the longitudinal passageways; deflating said balloon to its collapsed condition; rotating said balloon about its longitudinal axis; and reinflating said balloon to its expanded condition for a predetermined period of time to a sufficient size until each balloon member portion engages said stenosis to insure that the entire inner circumference of the stenosis has been engaged by at least one of said balloon member portions, while simultaneously perfusing blood through the longitudinal passageways.

2. The method of claim 1 wherein said first and second balloon member portions are disposed diametrically opposed across said flexible tubing.

3. The method of claim 1 wherein said means for communicating between said balloon and flexible tubing includes at least one pathway between said flexible tubing and said balloon.

4. The method dilation of claim 3 wherein said means for communicating between said balloon and flexible tubing includes a first pathway between said tubing and said first balloon member portion and a second pathway between said tubing and said second balloon member portion.

5. The method dilation catheter of claim 1 wherein said longitudinal passageways are larger in cross-sectional area than said flexible tubing.

6. The method of claim 1 wherein each of said longitudinal portions are bonded to less than one-half of the circumference of said flexible tubing.

* * * * *

UNITED STATES PATENT AND TRADEMARK OFFICE
CERTIFICATE OF CORRECTION

PATENT NO. : 5,433,706
DATED : July 18, 1995
INVENTOR(S) : Christopher L. Abiuso It is certified that error appears in the above-indentified patent and that said Letters Patent is hereby corrected as shown below:

Col. 6, line 17, delete "dilation"; line 23, delete "dilation catheter".

Signed and Sealed this

Twenty-sixth Day of November 1996

Attest:

BRUCE LEHMAN

Attesting Officer     Commissioner of Patents and Trademarks